(12) United States Patent
Macri et al.

(10) Patent No.: US 10,238,792 B1
(45) Date of Patent: Mar. 26, 2019

(54) CONNECTOR BRACKET IV POLE TOP

(71) Applicant: FIGHT LIKE MASON FOUNDATION, Belle River (CA)

(72) Inventors: Iain Macri, Belle River (CA); Chantelle Bacon, Belle River (CA)

(73) Assignee: Fight Like Mason Foundation, Belle River (CA)

( * ) Notice: Subject to any disclaimer, the term of this patent is extended or adjusted under 35 U.S.C. 154(b) by 0 days.

(21) Appl. No.: 15/869,981

(22) Filed: Jan. 12, 2018

Related U.S. Application Data

(60) Provisional application No. 62/563,023, filed on Sep. 25, 2017.

(51) Int. Cl.
| | |
|---|---|
| *F16M 11/00* | (2006.01) |
| *A61M 5/14* | (2006.01) |
| *F16M 11/42* | (2006.01) |
| *F16M 11/28* | (2006.01) |

(52) U.S. Cl.
CPC .......... *A61M 5/1415* (2013.01); *F16M 11/28* (2013.01); *F16M 11/42* (2013.01); *A61M 2205/59* (2013.01)

(58) Field of Classification Search
CPC .................................. A61M 5/14; F16M 13/02
See application file for complete search history.

(56) References Cited

U.S. PATENT DOCUMENTS

| | | | | |
|---|---|---|---|---|
| 2,077,107 | A * | 4/1937 | Grundman | A47G 33/105 362/392 |
| 7,556,226 | B2 * | 7/2009 | Muncie | A61M 5/1415 248/176.1 |
| 8,823,629 | B2 * | 9/2014 | Bae | G09M 3/3688 345/100 |
| 2009/0294604 | A1 * | 12/2009 | Sunderland | A61M 5/1415 248/124.1 |

* cited by examiner

*Primary Examiner* — Amy J. Sterling
(74) *Attorney, Agent, or Firm* — Ridout & Maybee LLP

(57) ABSTRACT

An intravenous (IV) pole assembly comprising: an IV pole having a pole, a plurality of hooks mounted to the pole, and a base with a plurality of wheels, wherein the plurality of hooks are for holding a container of intravenous fluid; and a decorative equipment including a decorative element and a connector bracket attached to the decorative element, the connector bracket for mounting on a top of the pole, the connector bracket comprises a shaft that defines a plurality of slots on one end of the shaft.

21 Claims, 6 Drawing Sheets

CONNECTOR BRACKET IV POLE TOP

CROSS-REFERENCE TO RELATED APPLICATION

The present application claims priority from U.S. provisional patent application No. 62/563,023, filed Sep. 25, 2017, the entire contents of which are hereby incorporated by reference into the DETAILED DESCRIPTION OF EXAMPLE EMBODIMENTS, herein below.

FIELD

Example embodiment relate generally to an intravenous (IV) pole assembly and, for example, to an IV pole connector bracket for mounting on top of an IV pole.

BACKGROUND

With the advancement of society system, intravenous (IV) poles are commonly used in hospitals for holding a container of IV fluid suspended above a patient. Such poles are mobile in that they have wheels so as to move along when the patient is walking.

Although arrangements of this type have generally been satisfactory for their intended purposes, one example problem which has been encountered is that, the size, shape, look, and medical treatment may be intimidating and cause much apprehension with intravenous injection devices in young patients. Such apprehension can be the result from unfamiliar surroundings and equipment as well as unfamiliar ways of doing things and sometimes painful medical treatments.

Accordingly, an assembled IV pole is desirable for young patients to reduce the intimidation created by the medical equipment and eliminate the apprehension from medical treatments in hospitals, surgery centers and home care.

As well, there are opportunities to mount additional items to IV poles to provide additional decorative or functional features.

SUMMARY

Embodiments of the present disclosure provide a connector bracket for an IV pole by alleviating children's anxiety and apprehension of painful medical treatments.

An example embodiment is an intravenous (IV) pole assembly comprising: a decorative equipment of colorful design; and a supporter having a pole, a plurality of hooks, and a base with a plurality of caster wheels, wherein the plurality of hooks are for holding a container of intravenous fluid, the decorative equipment is mountable on top of the supporter, the connector bracket comprises a shaft that defines a plurality of slots on one end of the shaft.

Another example embodiment is an intravenous (IV) pole assembly comprising: a supporter having a pole, a plurality of hooks mounted to the pole, and a base with a plurality of wheels, wherein the plurality of hooks for holding a container of intravenous fluid; and a decorative equipment including a decorative element and a connector bracket attached to the decorative element, the connector bracket for mounting on a top of the pole, the connector bracket comprises a shaft that defines a plurality of slots on one end of the shaft.

Another example embodiment is a decorative equipment for mounting on a top of an intravenous (IV) pole, the decorative equipment comprising: a connector bracket comprising a shaft that defines a plurality of slots on one end of the shaft; and a decorative element attached to the connector bracket.

BRIEF DESCRIPTION OF THE DRAWINGS

Reference will now be made, by way of example, to the accompanying drawings which show example embodiments, and in which.

Similar reference numerals may have been used in different figures to denote similar components.

DETAILED DESCRIPTION OF EXAMPLE EMBODIMENTS

The present disclosure generally provides an intravenous (IV) pole assembly with decorative equipment for securely holding a container of intravenous fluid above a patient, and for providing an atmosphere of fun to distract children from thinking about unpleasant experience and anxiety about taking intravenous injection.

Figure 1:
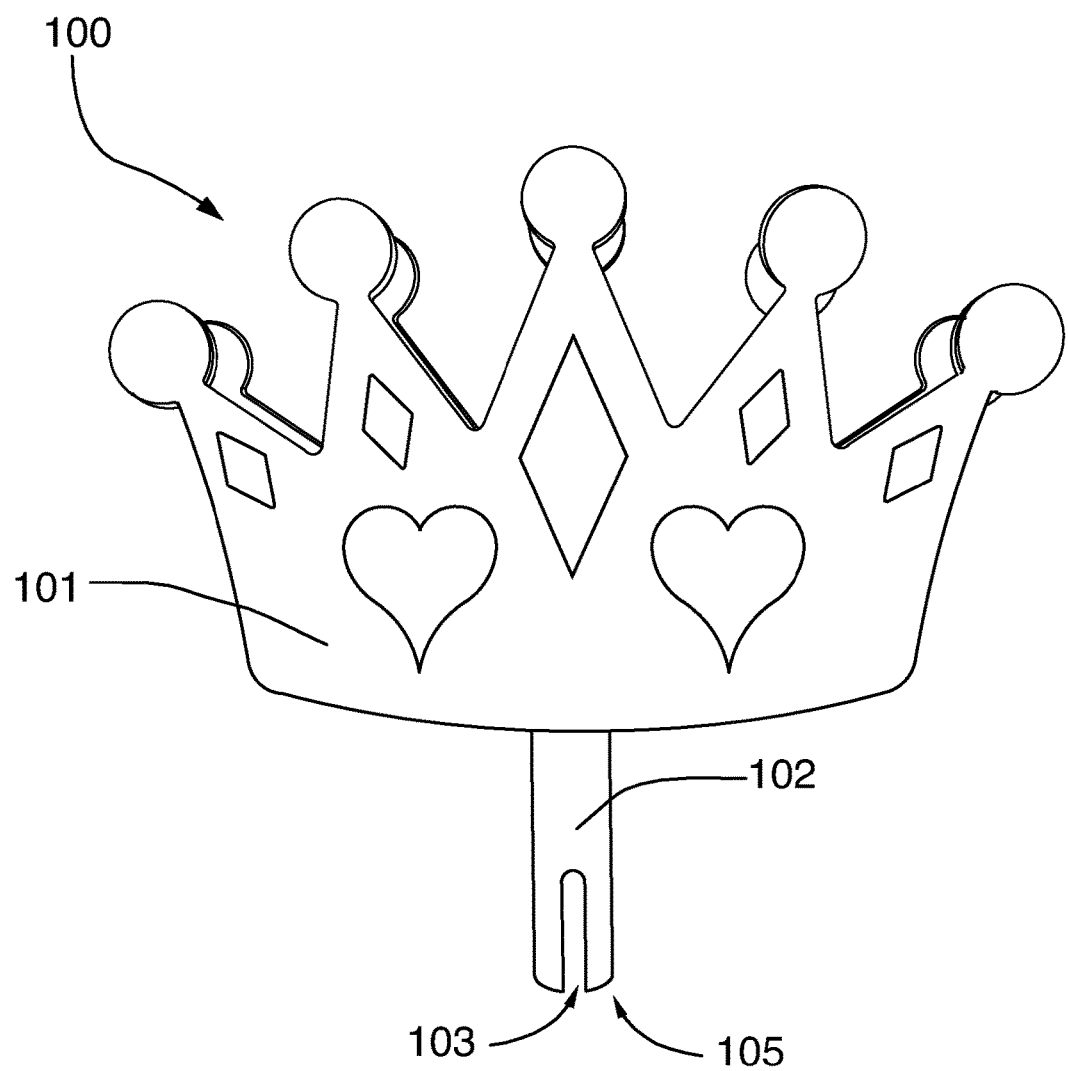
FIG. 1 illustrates a front view of a decorative equipment being mounted on a supporter according to an example embodiment.

Referring to FIG. 1, a decorative equipment 100 for attachment onto the top of an IV pole will be described in greater detail. As shown in FIG. 1, the decorative equipment 100 includes a decorative element such as a plurality of plaques 101 (e.g., two plaques 101 as shown), and a connector bracket 105 such as a shaft 102 defining a plurality of slots 103 on one end (e.g., bottom end) shown in FIGS. 5A, 5B, 5C, and 5D. On the other end (e.g., top end) of the shaft 102, there is attached the plaques 101. As shown in FIG. 1, each plaque 101 can be designed with the shape of a decorative element such as a colorful crown that may help to alleviate children's feeling of painful medical treatments. In an example embodiment, the shaft 102 acts as a removably mountable connector bracket between the IV pole and the plaques 101.

Figure 2:
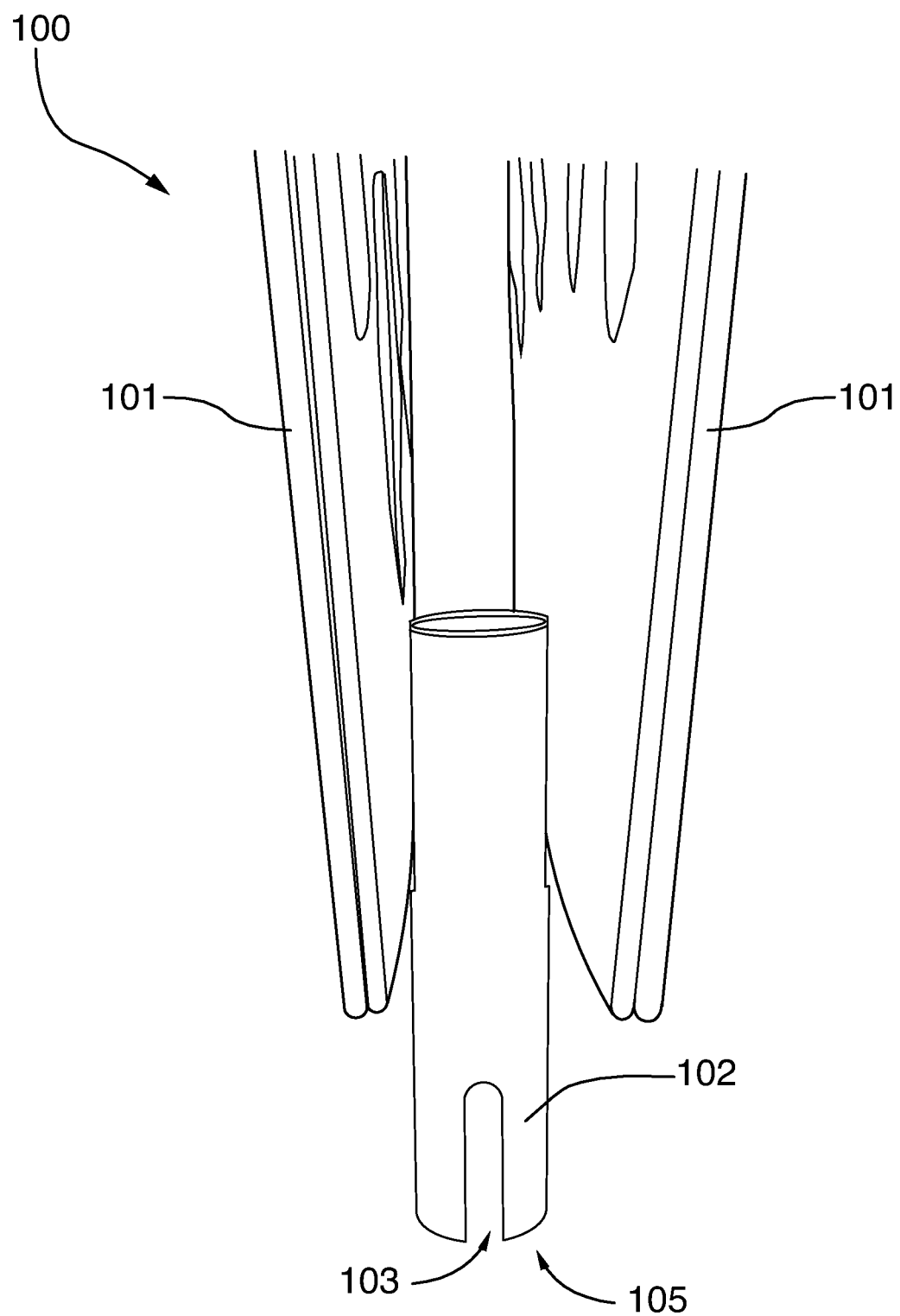
FIG. 2 illustrates a partial side view of the decorative equipment of FIG. 1.

FIG. 2 illustrates an example embodiment of the decorative equipment 100 wherein the number of the plaques 101 is two. In an example embodiment, the two plaques 101 are substantially identical in shape, are generally flat and are parallel with each other. The plaques 101 are secured on both radial sides of the shaft 102 to be symmetrical with respect to the shaft 102. In an example embodiment, the plaques 101 are welded to the shaft 102. In other example embodiments, the plaques 101 are attached to the shaft 102 using suitable fasteners, adhesives, or connecting mechanisms.

With regard to the connector bracket 105, FIGS. 5A, 5B, 5C, and 5D show a structure of the shaft 102 from different views, in an example embodiment. The shaft 102 is hollow in an example embodiment, which is relatively lighter, uses less material, and eases the manufacture of the slots 103. Two symmetrical flat planes 501, 502 are located on a circumference of the shaft 102 at the top end of the shaft 102. In other words, the flat planes 501, 502 cut through an arc of the circumference of shaft 102, or in other words cut out a segment of the circumference of shaft 102. In an example embodiment, best shown in FIG. 5A, the flat planes 501, 502, do not affect the inner circumference of the shaft 102, for example, the inner circumference of the shaft 102 remains as a complete circle. The flat planes 501, 502 are parallel to an axis defined by the length of the shaft 102, in an example embodiment. In other example embodiments, the flat planes 501, 502 are bias angled relative to the axis defined by the length of the shaft 102.

The flat planes 501, 502 are located on opposite radial sides of the shaft 102 and are used to engage with the parallel plaques 101. The flat planes 501, 502 run from the top end of the shaft 102 to partway down the length of the shaft 102, without running along the entire length of the shaft 102. Such a configuration may help to secure a flat surface each of the plaques 101 onto a respective one of the two flat planes 501, 502 of the shaft 102, by having increased surface area contact compared to a purely cylindrical shaft. As well, the bottom end of the shaft 102 remains as a cylinder shape for mounting.

In one example embodiment, the number of the plaque(s) 101 may be one, two, three, four, or more. The plaques 101 may be used to produce a character from a cartoon which makes a realistic 3D visual effect of the shape. The shaft 102 can comprise one, two, three, four, or more of the flat planes 501, 502. In another embodiment, the plurality of plaques 101 may be replaced with a three-dimensional graphic pattern and/or shape.

Figure 4:
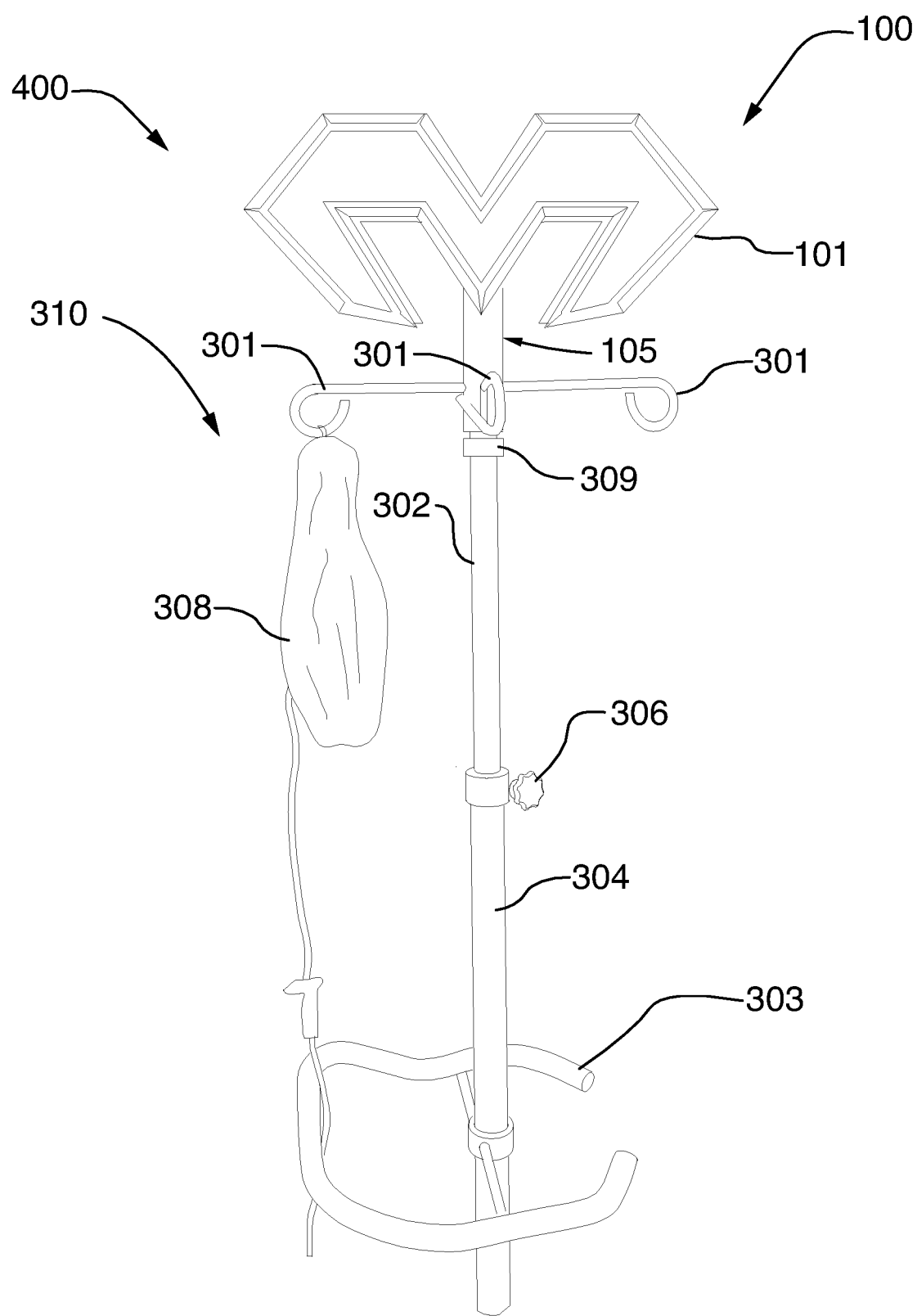
FIG. 4 illustrates a partial front view of an assembled IV pole according to another example embodiment.
Figure 5A:
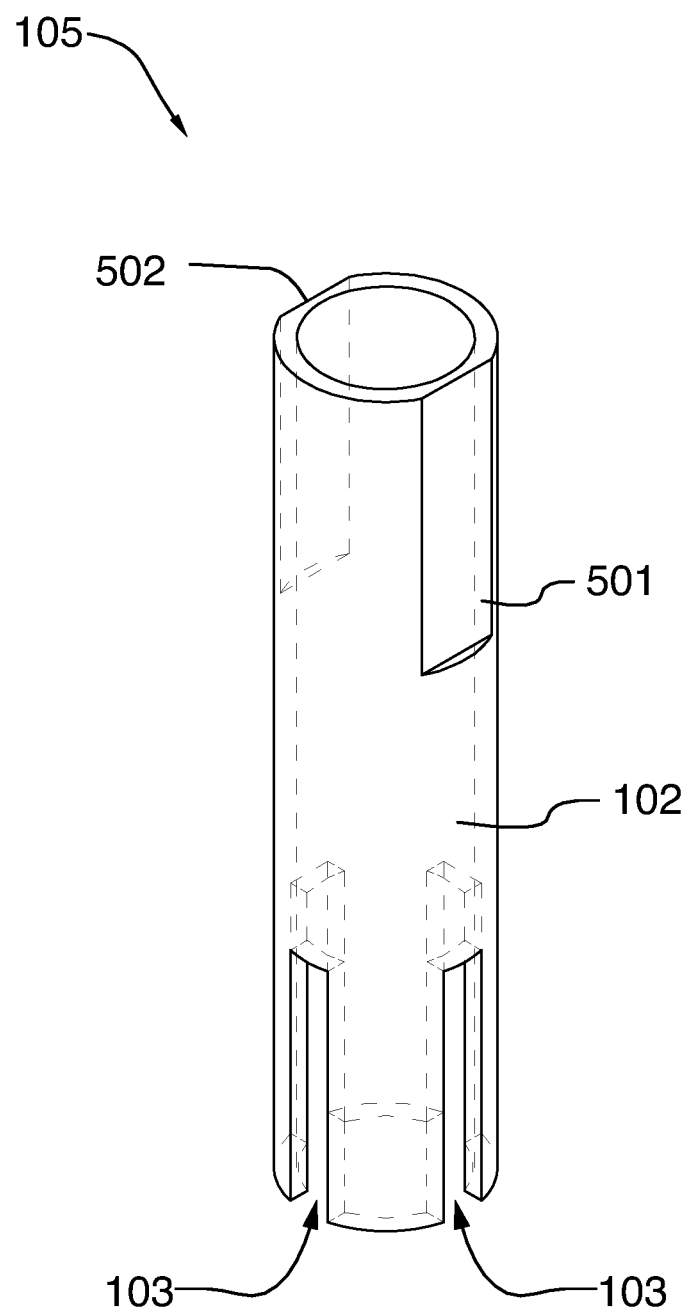
FIG. 5A illustrates a detail perspective view of a shaft of the decorative equipment according to an example embodiment.
Figure 5B:
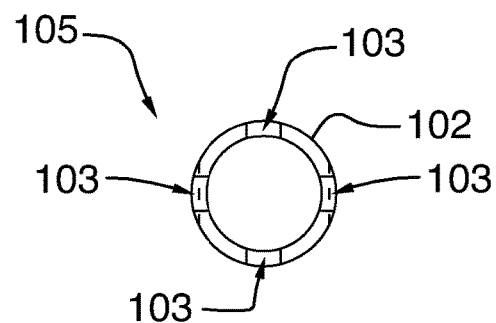
FIG. 5B illustrates a bottom view of the shaft of FIG. 5A.
Figures 5C, 5D:
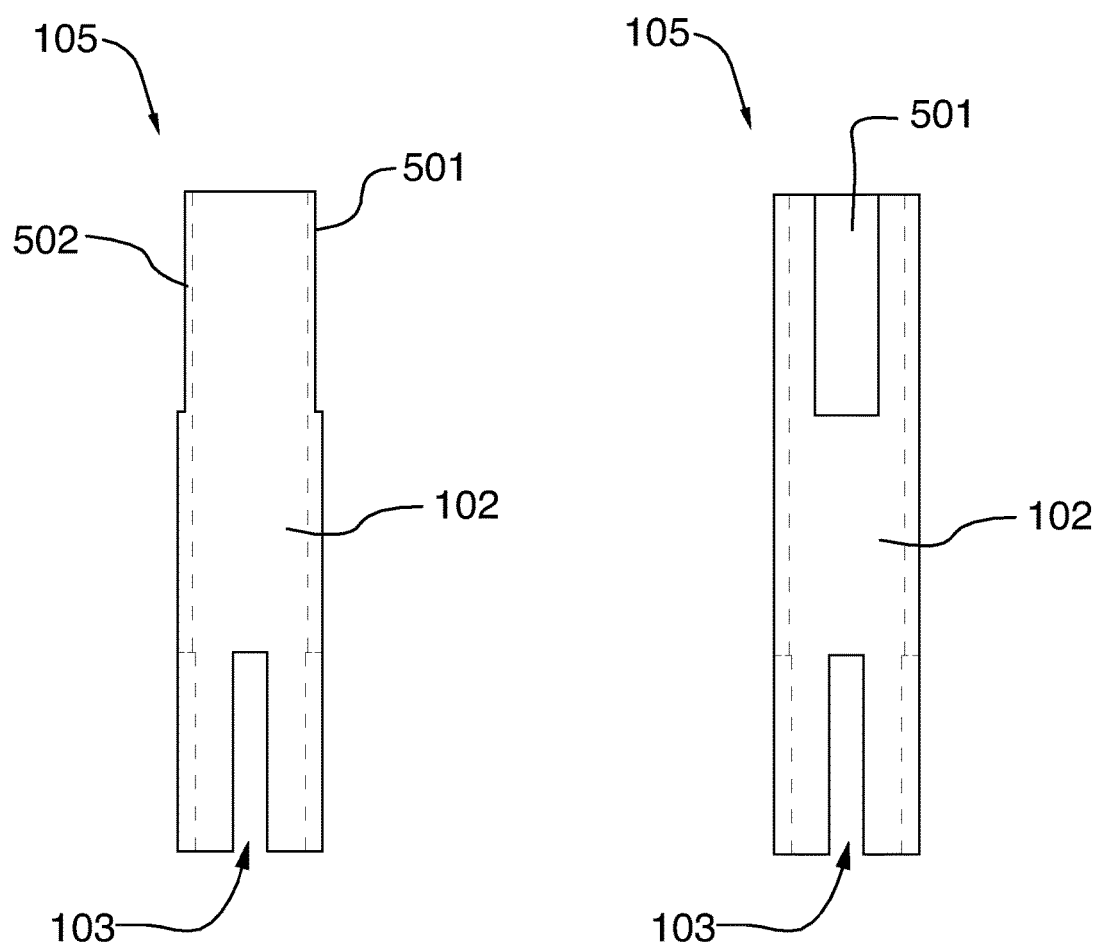
FIG. 5C illustrates a front view of the shaft of FIG. 5A.
FIG. 5D illustrates a side view of the shaft of FIG. 5A.

FIG. 4 illustrates a partial detail view of another example embodiment of an assembled IV pole 400. As shown in FIG. 4, the design of the plaque 101 is a "M" symbol. In one example embodiment, the shape of the plaque 101 can be designed according to children's preference which is not limited to the "M" symbol. For example, the designed shape may be various heroes characters from cartoon movies, such as Iron Man™, a super hero, etc., which may be popular to boys. Moreover, the designed shape for the plaque 101 may be characters from Disney™ movies, such as Snow White, Cinderella, Mickey Mouse™, and so on, that may be attractive to girls. In one example embodiment, the plaque 101 may include patients' identification information which may help staffs in hospital to recognize patients. In an example embodiment, a plurality of transversely extending hooks are attached to the plaque 101, for example, the plurality of hooks attached to the plaque 101 are designed at the upper end of the crown, or at the end of a Spider-man's finger. Several other shapes and configurations are possible in other example embodiments.

Figure 3:
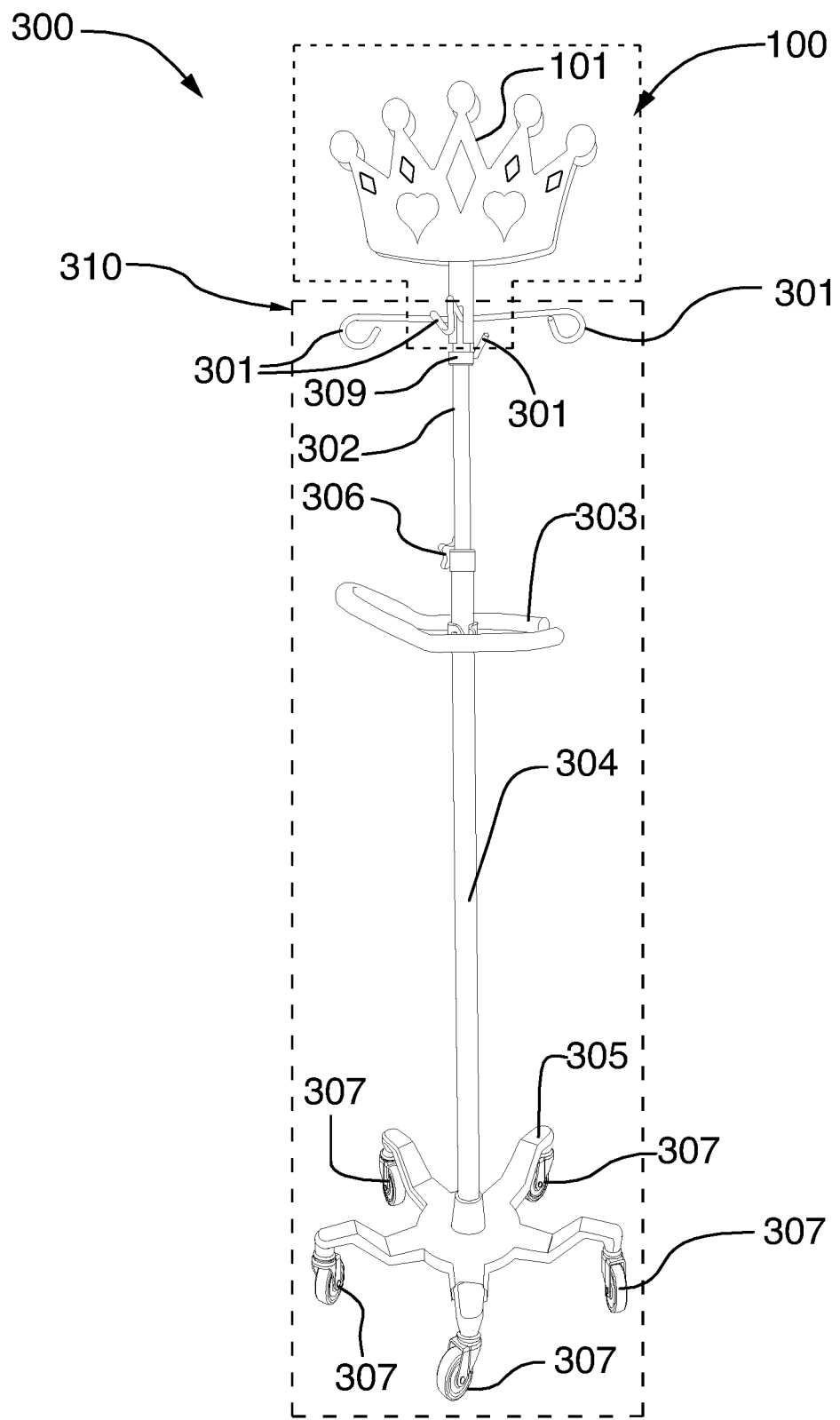
FIG. 3 illustrates a perspective view of an assembled IV pole with the decorative equipment according to an example embodiment.

Referring now to FIG. 3, an assembled IV pole 300 with the decorative equipment 100 can be made from an assembly of the component parts. The assembled IV pole 300 is used to hold a container of an intravenous fluid for the patient. The assembled IV pole 300 comprises the decorative equipment 100 (indicated by dotted line), and a supporter 310 (indicated by dotted line). In an example embodiment, the supporter 310 is an IV pole. The decorative equipment 100 is disposed on the top of the supporter 310. The supporter 310 comprises a plurality of hooks 301, an inner tube 302, an outer tube 304, a handle 303 attached to the outer tube 304, and a base 305 supporting the outer tube 304, and a plurality caster wheels 307 supporting the base 305. The inner tube 302 and the outer tube 304 can be collectively referred to as a pole. As shown in FIG. 3, the outer tube 304 extends from a low end secured on the base 305, to an upper end where the inner tube 302 is partially disposed therein with a telescoping relation. A cap 306 is secured to the top of the outer tube 304 by a set screw to adjust the height of the IV fluid suspended above a patient. The set screw can be used to engage the inner tube 302 by friction in an example embodiment. In other example embodiments, the inner tube 302 defines a plurality of holes (not shown) along its length, and the cap 306 comprises a spring plunger to engage one of the holes, locking the relative vertical positions of the tubes 302, 304. The IV fluid can be distributed to the patient using a natural mechanism such as gravity, and/or an artificial mechanism such as a pump or a valve. The wheels 307 allow the container to be readily moved around, for example by the patient manipulating the handle 303.

With reference to the FIG. 3, FIG. 5A, FIGS. 5B, 5C and 5D, the number of the slots 103 of the decorative equipment 100 corresponds to a same number of the hooks 301 when mounted to the supporter 310. A slot width of each slot 103 generally corresponds to a width of each hook 301, e.g. slightly bigger. Each slot 103 runs longitudinally (axially) from the bottom end of the shaft 102, and are defined at different positions on a circumference of the shaft 102. In an example embodiment, the slots 103 run from the bottom end of the shaft 102 to partway up the length of the shaft 102, without running along the entire length of the shaft 102. The hooks 301 are accommodated into the slots 103 to allow the structure of the decorative equipment 100 to be placed over the structure of the supporter 310. The top of the inner tube 302 is positioned inside the shaft 102 of the decorative equipment 100 to assemble the decorative equipment 100 and the supporter 310 together. A diameter of the shaft 102 generally corresponds to a diameter of the top of the inner tube 302, e.g. slightly bigger. As may be appreciated, once installed the decorative equipment 100 is rotation locked, i.e. does not rotate, with respect to the top of the supporter 310. This is because each slot 103 engages a corresponding hook 301. The shaft 102 and the slots 103 are of a length so that the closed end of each slot 103 touches the corresponding hook 301.

In an example embodiment, the shaft 102 is removably mountable to the top of the inner tube 302 and can be slid on or off by moving the shaft 102 up or down in a vertical direction. In an example embodiment, the shaft 102 remains in place on the inner tube 302 using gravity. In an example embodiment, a fastener or other attachment mechanisms are used to further secure the shaft 102 to the top of the inner tube 302. An example fastener is a set screw.

In an example embodiment, the inner tube 302 defines a lip 309 that extends radially outward from the inner tube 302. In an example embodiment, the shaft 102 and the slots 103 are of a length such that the shaft 102 also rests on the lip 309, providing further vertical support to the decorative equipment 100.

In one example embodiment, any one, any part, or all of the hooks 301, the handle 303, and the base 305 with caster wheels 307 may be painted with respective color corresponding to respective color of the plaque 102. For example, in FIG. 3, the color of the crown can be the same as the color of the handle 303. The color of the base 305 is the same as the decoration on the crown, for example.

Referring again to FIG. 4, the bottom part of the assembled IV pole 400, not shown, is similar or the same as the assembled IV pole 300 of FIG. 3. An IV bag 308 or other container for IV fluid can be mounted to one of the hooks 301. In FIG. 4, the color of the hooks 301 and the color of the inner tube 302 can be the same as the color of outer edge of the "M" symbol, the color of the outer tube 304 and the base 305 can be the same as the color of interior of the "M" symbol. The children taking IV injections can move with the assembled IV pole which may help the children feel walking along with their dream heroes or their favorite cartoon characters, distracting the children from the stress of the painful experience. Such a design with impressive shape mounted on the top of the assembled IV pole may help to provide a relax environment with added fun for the children by alleviating the feeling of pressure of various medical treatment in hospital.

The plaques 101 are an example decorative element, and it can be appreciated that other decorative elements can be used in other example embodiments.

In other example embodiments, the decorative equipment 100 includes other items that are attached to one or more of the plaques 101, or items that can be used in replacement to one or more of the plaques 101. Examples of such items include a functional element such as a basket centrally mounted at its bottom to the top end of the shaft 102, or one or more hooks, or a computer tablet. Examples of such items include an electronic sign or animation, for example.

An example embodiment includes a method for assembling or manufacturing the decorative equipment 100. An example embodiment includes a method for assembling or manufacturing the IV pole assembly. An example embodiment includes a use of the IV pole assembly.

Certain adaptations and modifications of the described embodiments can be made. Therefore, the above discussed embodiments are considered to be illustrative and not restrictive.

What is claimed is:

1. An intravenous (IV) pole assembly comprising:
   a supporter having a pole, a plurality of hooks mounted to the pole, and a base with a plurality of wheels, wherein the plurality of hooks are for holding a container of intravenous fluid; and
   a decorative equipment including a decorative element and a connector bracket attached to the decorative element, the connector bracket for mounting on a top of the pole, the connector bracket comprises a shaft that defines a plurality of slots on one end of the shaft,
   wherein the shaft includes one or more flat planes on a circumference of the shaft.

2. The intravenous pole assembly of claim 1, wherein a number of the slots on the shaft engages a same number of the hooks of the plurality of hooks when mounted on the top of the pole.

3. The intravenous pole assembly of claim 1, wherein a diameter of the shaft generally matches a diameter of the top of the pole.

4. The intravenous pole assembly of claim 1, wherein a slot width of each of the slots generally matches a respective width of a corresponding hook of the plurality of hooks when assembled.

5. The intravenous pole assembly of claim 1, wherein the decorative element comprises two or more plaques, each substantially identical in shape, and each mounted on opposing sides of the shaft.

6. The intravenous pole assembly of claim 1, wherein the shaft includes one or more flat planes on a circumference of the shaft.

7. The intravenous pole assembly of claim 1, wherein the decorative element comprises one or more plaques.

8. The intravenous pole assembly of claim 7, wherein the one or more flat planes on the circumference of the shaft are each for engaging with one of the plaques.

9. The intravenous pole assembly of claim 7, wherein the one or more plaques each have a flat surface to each respectively engage one of the flat planes on the shaft.

10. The intravenous pole assembly of claim 1, wherein the connector bracket is removably mountable to the top of the pole.

11. The intravenous pole assembly of claim 1, wherein each slot runs longitudinally along a length of the shaft.

12. The intravenous pole assembly of claim 1, wherein the decorative element is mounted at another end of the shaft opposite the one end of the shaft.

13. The intravenous pole assembly of claim 1, wherein the shaft is rotation locked when mounted on the top of the pole due to interaction of the slots with the plurality of hooks.

14. A decorative equipment for mounting on a top of an intravenous (IV) pole, the decorative equipment comprising:
    a connector bracket comprising a shaft that defines a plurality of slots on one end of the shaft; and
    a decorative element attached to the connector bracket, wherein the shaft includes one or more flat planes on a circumference of the shaft.

15. The decorative equipment of claim 14, wherein the IV pole further comprises a pole, a plurality of hooks mounted to the pole, and a base with a plurality of wheels, wherein the plurality of hooks are for holding a container of intravenous fluid, wherein a number of the slots on the shaft engages a same number of the hooks of the plurality of hooks when mounted on the top of the supporter.

16. The decorative equipment of claim 14, wherein the decorative element comprises one or more plaques.

17. The decorative equipment of claim 14, wherein the decorative element comprises two or more plaques, each substantially identical in shape, and each mounted on opposing sides of the shaft.

18. The decorative equipment of claim 14, wherein each slot is defined longitudinally from one end of the shaft to partway along a length of the shaft.

19. The decorative equipment of claim 18, wherein each slot is positioned on a circumference of the shaft.

20. The decorative equipment of claim 14, wherein the one or more flat planes are defined longitudinally from one end of the shaft to partway along a length of the shaft.

21. The decorative equipment of claim 14, wherein the one or more flat planes are parallel to a central axis defined by a length of the shaft.

\* \* \* \* \*